US011260400B2

(12) United States Patent
Zhu et al.

(10) Patent No.: US 11,260,400 B2
(45) Date of Patent: Mar. 1, 2022

(54) INCLINED MAGNETIC HOLDER

(71) Applicant: Nanjing GenScript Biotech Co., Ltd., Nanjing (CN)

(72) Inventors: Jinxin Zhu, Nanjing (CN); Hong Qian, Nanjing (CN); Weijuan Han, Nanjing (CN); Ruina He, Nanjing (CN); Tao Bai, Nanjing (CN); Chao Wang, Nanjing (CN)

(73) Assignee: Nanjing GenScript Biotech Co., Ltd., Jiangsu (CN)

( * ) Notice: Subject to any disclaimer, the term of this patent is extended or adjusted under 35 U.S.C. 154(b) by 96 days.

(21) Appl. No.: 16/760,552

(22) PCT Filed: Oct. 30, 2018

(86) PCT No.: PCT/CN2018/112628
§ 371 (c)(1),
(2) Date: Apr. 30, 2020

(87) PCT Pub. No.: WO2019/085890
PCT Pub. Date: May 9, 2019

(65) Prior Publication Data
US 2021/0069726 A1    Mar. 11, 2021

(30) Foreign Application Priority Data

Oct. 30, 2017   (CN) .......................... 201711033873.2

(51) Int. Cl.
*B03C 1/033*        (2006.01)
*B03C 1/28*         (2006.01)
(Continued)

(52) U.S. Cl.
CPC .............. *B03C 1/0332* (2013.01); *B01L 9/06* (2013.01); *B03C 1/288* (2013.01);
(Continued)

(58) Field of Classification Search
USPC .......................................... D24/227, 229, 230
See application file for complete search history.

(56) References Cited

U.S. PATENT DOCUMENTS

| 4,895,650 | A | * | 1/1990 | Wang ........................ B01L 9/06 |
| | | | | 210/222 |
| 5,098,663 | A | * | 3/1992 | Berthold ................... B01L 9/06 |
| | | | | 422/561 |

(Continued)

FOREIGN PATENT DOCUMENTS

| CN | 204999920 U | 1/2016 |
| CN | 206121919 U | 4/2017 |
| CN | 206359540 U | 7/2017 |

OTHER PUBLICATIONS

PCT/CN2018/112628 International Search Report and Written Opinion, dated Jan. 30, 2019 (6 pages).
(Continued)

*Primary Examiner* — David C Mellon
(74) *Attorney, Agent, or Firm* — Klarquist Sparkman, LLP

(57) ABSTRACT

An inclined magnetic holder comprises a magnetic base and a centrifuge tube support plate. The centrifuge tube support plate has centrifuge tube support holes. The magnetic base comprises a first bottom plate, a fixing plate, and two first-side support plates. Respective top portions of the two first-side support plates are provided with a position-locating slot. Two ends of the centrifuge tube support plate are respectively provided with a position-locating protruding block. The centrifuge tube support holes are evenly and linearly distributed on the centrifuge tube support plate. An elastic circular engagement component for holding a centrifuge tube is provided inside the centrifuge tube support holes. A block magnet is fixed to the fixing plate below and corresponding to each of the centrifuge tube support holes.
(Continued)

A north pole or south pole surface of the block magnet faces the centrifuge tube and is parallel to an axis of the centrifuge tube.

20 Claims, 5 Drawing Sheets

(51) Int. Cl.
*B01L 9/06* (2006.01)
*C07K 1/14* (2006.01)
*H01F 1/057* (2006.01)

(52) U.S. Cl.
CPC ...... *B03C 2201/18* (2013.01); *B03C 2201/22* (2013.01); *B03C 2201/26* (2013.01); *C07K 1/14* (2013.01); *H01F 1/057* (2013.01)

(56) References Cited

U.S. PATENT DOCUMENTS

| | | | | |
|---|---|---|---|---|
| 5,571,481 | A * | 11/1996 | Powell | B03C 1/288 422/562 |
| D414,273 | S * | 9/1999 | Smith | D24/227 |
| 5,985,219 | A * | 11/1999 | Lind | B01L 9/06 422/562 |
| 6,193,892 | B1 * | 2/2001 | Krueger | B03C 1/288 210/695 |
| 8,211,386 | B2 * | 7/2012 | Talmer | B65D 21/0233 422/560 |
| 9,144,801 | B2 * | 9/2015 | Johnson | B01L 9/06 |
| D781,437 | S * | 3/2017 | Valley | D24/227 |
| 2004/0124109 | A1 * | 7/2004 | Hassinen | G01N 35/04 206/443 |
| 2009/0028759 | A1 * | 1/2009 | Su | B03C 1/288 422/400 |
| 2010/0264090 | A1 * | 10/2010 | Ellis | B03C 1/0332 210/695 |
| 2014/0305849 | A1 * | 10/2014 | Fu | B01L 9/06 209/215 |
| 2015/0090664 | A1 * | 4/2015 | Nokleby | B03C 1/14 210/695 |
| 2019/0299215 | A1 * | 10/2019 | Guttman | B03C 1/0332 |

OTHER PUBLICATIONS

PCT/CN2018/112628 English translation of International Search Report, dated Jan. 30, 2019 (2 pages).

* cited by examiner

INCLINED MAGNETIC HOLDER

CROSS REFERENCE TO RELATED APPLICATIONS

This is the U.S. National Stage of International Application No. PCT/CN2018/112628, filed Oct. 30, 2018, which was published in Chinese under PCT Article 21(2), which in turn claims the benefit of Chinese Patent Application No. 201711033873.2, filed Oct. 30, 2017.

FIELD

The present disclosure is related to an inclined magnetic holder device, and particularly, to a magnetic holder for magnetic bead purification, and belongs to the technical field of biological device for protein and nucleic acid purification etc.

BACKGROUND

Magnetic bead purification is to use a magnetic holder to separate magnetic beads by the magnetic field to achieve the purpose of separating and purifying cells, proteins or nucleic acids. Compared with a commonly used precipitation method, centrifugation method and column membrane method, the magnetic bead method has the characteristics of high extraction efficiency, fast separation speed, and simple equipment. A process of magnetic separation is roughly as follows: magnetic beads that can combine to-be-separated samples are added to a centrifugal tube with the to-be-separated samples, mixed well and incubated, and placed on the magnetic holder; at this time, the magnetic beads are attracted to a tube wall of the centrifugal tube on the side of the magnet under the magnetic field generated by the magnet of the magnetic holder, and non-adsorbed solution is then removed or poured to achieve separation of the to-be-separated samples from other samples.

Although the existing magnetic holder on the market can meet the demand of some customers, there are still many shortcomings, for example as follows.

1) Most magnetic holders are designed as an integrated structure; the magnetic base and the centrifugal tube supporting plate cannot be separated; when performing magnetic separation, mixing operation, and waste liquid pouring, an operator needs to repeatedly transfer a single centrifugal tube one by one. It is not easy to realize synchronous operation of all centrifugal tubes.

2) Centrifugal tubes suitable for the existing magnetic holder have a single size; to meet centrifugal tubes with different capacities, magnetic holders of different sizes are required to be employed, which increases use cost and reduces working efficiency.

3) There is no measure to prevent the centrifugal tube from loosening or falling off during the process of flipping, shaking and pouring the waste liquid inclinedly, and the safety of the experimental operation cannot be guaranteed.

4) The polarity arrangement of the magnet is unreasonable. The magnetic polarities of adjacent magnets interfere with each other, which reduces the effect of the magnetic field. As a result, the adjacent magnets will reduce the effect of magnets corresponding to neighboring centrifugal tubes absorbing the magnetic beads in the centrifugal tube.

5) The magnet and the centrifugal tube are arranged in a vertical direction, which leads to a low adsorption efficiency of magnetic beads in the centrifugal tube during the purification process.

6) The shape and position of the magnet are not optimized, making it difficult for the magnetic beads at the bottom of the centrifugal tube to be adsorbed to the magnet far above the bottom of the centrifugal tube, or making it difficult for all the magnetic beads to be absorbed to the magnet near the bottom of the centrifugal tube, or making it difficult for the magnetic beads in the liquid of the upper part of the centrifugal tube to be absorbed to the magnet away from the upper part of the centrifugal tube, leading to loss of magnetic beads when removing or pouring the waste liquid.

7) Most of the existing magnetic holder adopts a dual-row centrifugal tube layout. To improve the efficiency of removing waste liquid, when the supernatant is completely removed in a flipping manner, cross-contamination of samples between centrifugal tubes may occur.

SUMMARY OF THE INVENTION

To solve the above existing problem of using a magnetic holder for magnetic bead purification, the present invention provides an inclined magnetic holder device.

The following technical solutions are used in the present invention: an inclined magnetic holder device, including a magnetic base and a centrifugal tube supporting plate having centrifugal tube supporting holes thereon, where the magnetic base includes a first baseplate, a fixing plate disposed on the first baseplate and two first side supporting plates located at two sides of the fixing plate; positioning grooves are respectively provided on the top of the two first side supporting plates; bottom surfaces of the positioning grooves are disposed inclinedly; positioning bumps for engaging in the positioning grooves are respectively provided at two ends of the centrifugal tube supporting plate; the centrifugal tube supporting holes are evenly distributed on the centrifugal tube supporting plate in a straight line; annular elastic buckles for fixing a centrifugal tube are installed in the centrifugal tube supporting holes; magnet blocks are respectively fixed on positions of the fixing plate corresponding to the underneath of all of the centrifugal tube supporting holes; the magnet block below each centrifugal tube supporting hole respectively corresponds to each centrifugal tube, and a surface where the N or S pole of the magnet block is located faces the centrifugal tube and is parallel to the axis of the centrifugal tube.

The inclined magnetic holder device further includes a nonmagnetic base, where the nonmagnetic base includes a second baseplate and two second side supporting plates fixed at two sides of the second baseplate, and positioning grooves engaging with the positioning bumps are respectively provided on the top of the two second side supporting plates.

A magnet sheet A is provided on a bottom surface of the positioning groove, a magnet sheet B for being absorbed with the magnet sheet A is provided on a bottom surface of the positioning bump, and adjacent surfaces of the magnet sheet A and the magnet sheet B have opposite polarities.

The positioning groove has a cross section of a trapezoidal groove with a larger top and a smaller bottom, two sides of the trapezoidal groove are in the shape of bevels, the two sides of the positioning bumps are provided with guiding bevels engaged with the bevels of the trapezoidal groove, and blocking surfaces fit with a side plate blocking part are provided on two sides of the positioning bump on the centrifugal tube supporting plate.

A centrifugal tube positioning hole is provided on a position of the first baseplate and the second baseplate corresponding to the underneath of each of the centrifugal tube supporting holes.

The centrifugal tube positioning hole is a gourd-shaped hole, the gourd-shaped hole includes two circular holes with different diameters connected together in a front-to-back direction, and the axis of the two circular holes is parallel to the axis of the centrifugal tube.

The magnet blocks with the N pole facing the centrifugal tube and the magnet blocks with the S pole facing the centrifugal tube are laid out in a manner where adjacent magnet blocks have opposite magnetic polarities.

The material of the magnet block is a strong Nd—Fe—B magnet N52, and the surface of the magnet block is provided with a single-layer nickel bright silver anticorrosive layer.

The fixing plate is disposed inclinedly on the first baseplate; an angle of the fixing plate is the same as that of the centrifugal tube installed in the centrifugal tube supporting plate; the magnet block is L-shaped, the N or S pole of the L-shaped magnet block is located on an outer side of a vertical end of the L-shaped magnet block, the outer side of the vertical end of the L-shaped magnet block and the fixing plate are located in the same plane, and the lateral end of the L-shaped magnet block is fixed on the first baseplate.

An angle between the fixing plate and a horizontal surface is 90° to 135°.

The fixing plate and the first baseplate are integratedly connected together.

The material of the first baseplate, the fixing plate, the first side supporting plate, the centrifugal tube supporting plate, the second baseplate, and the second side supporting plate is all ABS plastic.

The elastic buckle includes an annular ring, locking feet and clamping feet are evenly and distributed on the annular ring at intervals the locking feet protrude outward from the annular ring for fixing on the centrifugal tube supporting holes, and the clamping feet protrude inwards the annular ring for fixing the centrifugal tube.

The numbers of the locking feet and the clamping feet in the elastic buckle are greater than or equal to 3, and the material of the elastic buckles is PA66.

The positioning bumps on the two ends of the centrifugal tube supporting plate are respectively provided with handles.

A bolt hole is provided on the first side supporting plate, and the two first side supporting plates are fixedly installed on the two sides of the fixing plate via bolts respectively.

The number of the holes of the centrifugal tube supporting plate is 1 to 20, and the number of the magnet blocks is equal to that of the holes of the centrifugal tube supporting plate.

The number of the holes of the centrifugal tube supporting plate is 4 to 12.

Beneficial effects of the present invention are that: in the present invention, when magnetic bead separation is performed, magnetic beads that can combine to-be-separated samples are added to a centrifugal tube with the to-be-separated samples; the centrifugal tubes are fixed in centrifugal tube supporting holes via elastic buckles; positioning bumps on the two ends of a centrifugal tube supporting plate are respectively installed to positioning grooves on two first side supporting plates, thereby easily assembling the centrifugal tube supporting plate with the centrifugal tube onto a magnetic base; because bottom surfaces of the positioning grooves are inclinedly set, the assembled centrifugal tube supporting plate and centrifugal tube are inclinedly set; a surface where the N or S pole of the magnet block is located faces the centrifugal tube and is parallel to the axis of the centrifugal tube, thus increasing the absorption force of the magnetic beads. Assembly or separation of the centrifugal tube supporting plate and the magnetic base can be easily achieved in the present invention. A user may synchronously perform magnetic separation, mixing operation, and waste liquid pouring in the purification of all samples and protein transfer after purification. The centrifugal tube supporting holes are evenly distributed on the centrifugal tube supporting plate in a straight line. The centrifugal tubes are arranged in a single row, and all waste liquid can be removed at one time by overall flipping, thereby greatly increasing efficiency of removing waste liquid, and avoiding sample cross-contamination between centrifugal tubes during the flipping process.

Preferably, a nonmagnetic base is further provided in the present invention. When magnetic bead release operation is performed, positioning bumps at two ends of the centrifugal tube supporting plate are respectively installed in the positioning grooves on the two second side supporting plate, thereby easily implementing magnetic bead release operation by combining the centrifugal tube supporting plate on the nonmagnetic base.

Preferably, it is convenient to assemble the centrifugal tube supporting plate with the magnetic base or the nonmagnetic base through the absorption force of the magnets A and B.

Preferably, a guiding bevel on a positioning bump of the centrifugal tube supporting plate is fit with a bevel guide of a trapezoidal positioning groove, which more facilitates the assembly of the centrifugal tube supporting plate and the magnetic base or the nonmagnetic base, and a blocking surface may prevent the centrifugal tube supporting plate from moving laterally.

Preferably, the centrifugal tube positioning holes on a first base and a second base facilitate positioning of the centrifugal tubes.

Preferably, the gourd-shaped centrifugal tube positioning hole facilitates positioning of centrifugal tubes with different diameters, and small and big holes of the gourd-shaped holes are selected according to actual needs.

Preferably, the magnet blocks with the N pole facing the centrifugal tube and the magnet blocks with the S pole facing the centrifugal tube are laid out in a manner where adjacent magnet blocks have opposite magnetic polarities. The layout manner is N-S-N-S-N-S or S-N-S-N-S-N, which greatly increases the absorption efficiency of magnetic beads and reduces loss of magnetic beads.

Preferably, a magnet block using strong Nd—Fe—B magnet N52 has the characteristics of strong magnetic force and large adsorption force, which makes the magnetic bead separation more thorough.

Preferably, an L-shaped magnet block is used to facilitate inclined arrangement on the fixing plate. The fixing plate is designed inclinedly. The overall structure is simple and lightweight, which is convenient for installation and flexible operation.

Preferably, the magnetic base and the nonmagnetic base that are made of ABS plastic have advantages of robust, lightweight, and low cost.

Preferably, the elastic buckles are locked and fixed on the centrifugal tube supporting plate by the locking feet. The elastic buckles clamp and fix the centrifugal tubes with different sizes with the clamping feet. The centrifugal tubes within a size range of 15 ml to 100 ml are applicable. During the process of flipping, shaking and pouring the waste liquid inclinedly, the centrifugal tube is prevented from loosening or falling off, and the centrifugal tubes are easily taken out and installed.

Preferably, the centrifugal tube supporting plate is provided with a handle for installing, assembling, and disassembling the centrifugal tube supporting plate.

Preferably, the first side supporting plate is provided with a bolt hole. According to actual height needs, the bolt can be installed in a suitable bolt hole so as to connect the first side supporting plate and the fixing plate.

BRIEF DESCRIPTION OF THE INVENTION

DETAILED DESCRIPTION OF THE INVENTION

The present invention is described in detail below with reference to the drawings and specific embodiments. It should be understood that the following detailed description is merely exemplary and illustrative, and should not limit the present invention.

Figure 1:
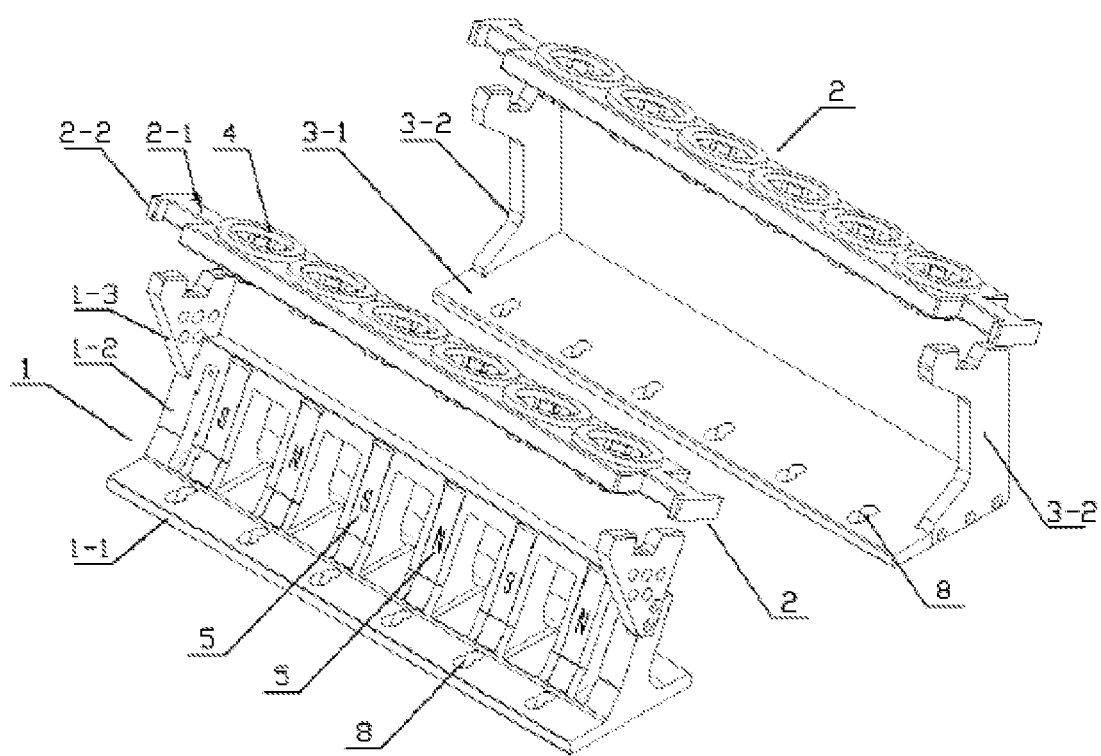
FIG. 1 is a schematic structural diagram of an embodiment of an inclined magnetic holder device according to the present invention.
Figure 2:
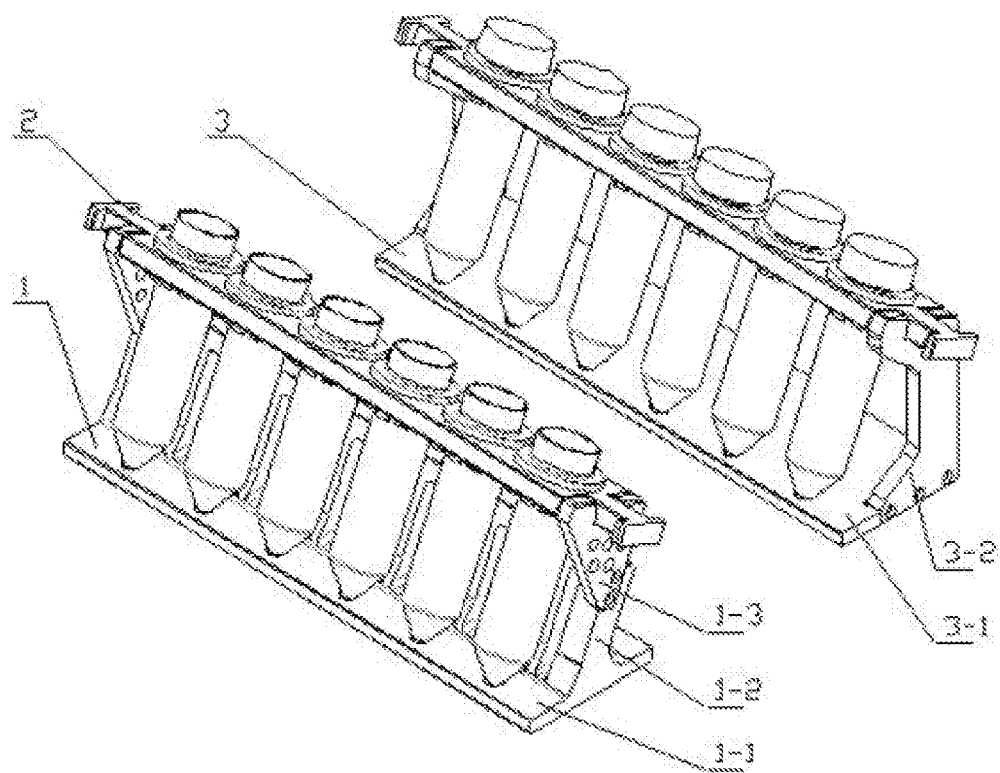
FIG. 2 is a use state diagram of FIG. 1.
Figure 3:
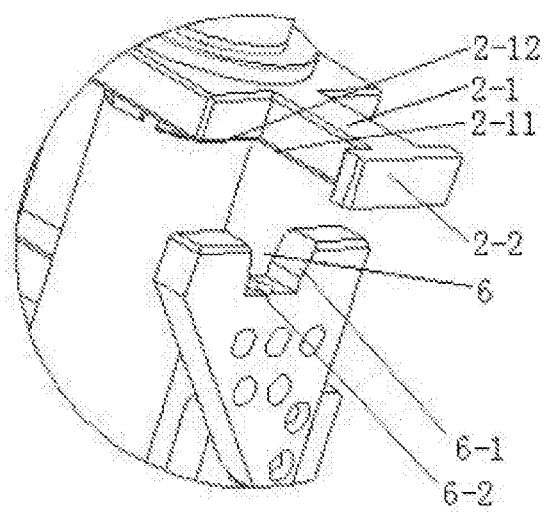
FIG. 3 is an enlarged diagram of fitting of a first side supporting plate and a centrifugal tube supporting plate in FIG. 1.
Figure 4:
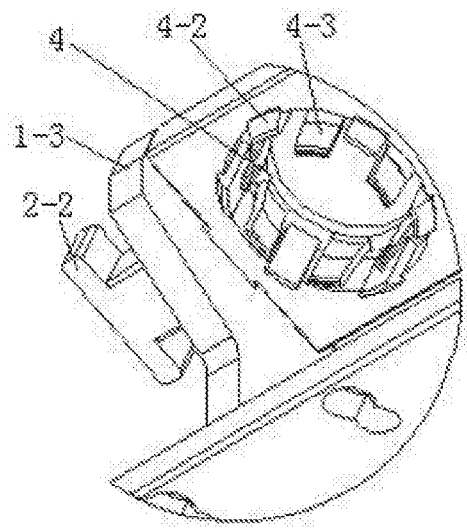
FIG. 4 is an enlarged diagram of an elastic buckle in FIG. 1.
Figure 5:
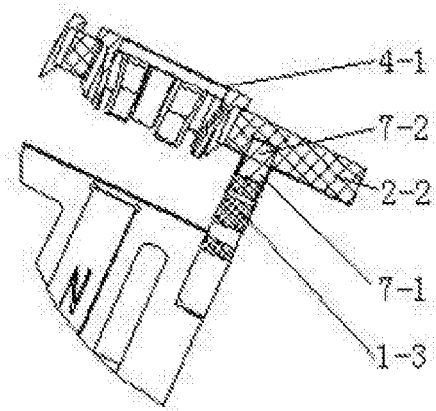
FIG. 5 is a sectional view of fitting of the first side supporting plate and the centrifugal tube supporting plate in FIG. 2.
Figure 6:
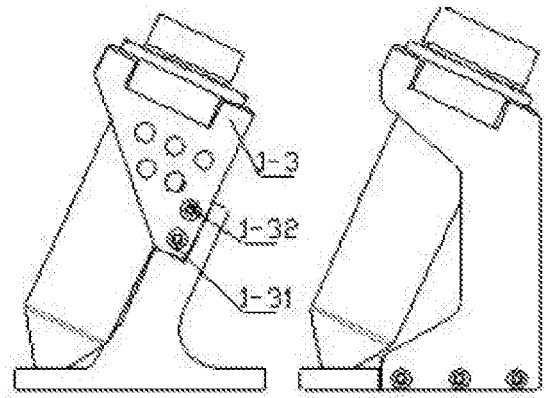
FIG. 6 is a right side view of FIG. 2.
Figure 7:
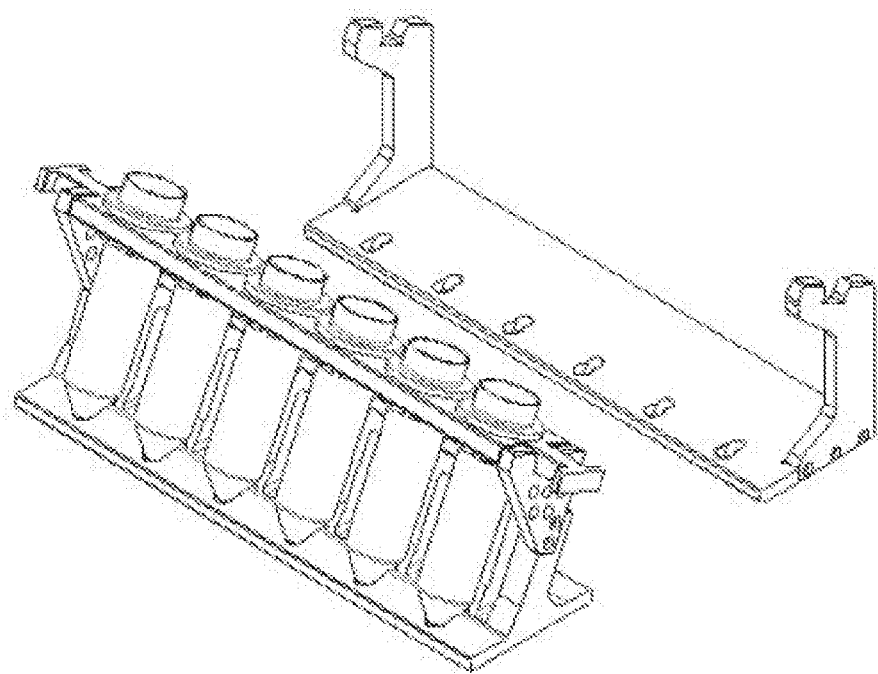
FIG. 7 is a working state diagram of magnetic beads of an inclined magnetic holder device according to the present invention.
Figure 8:
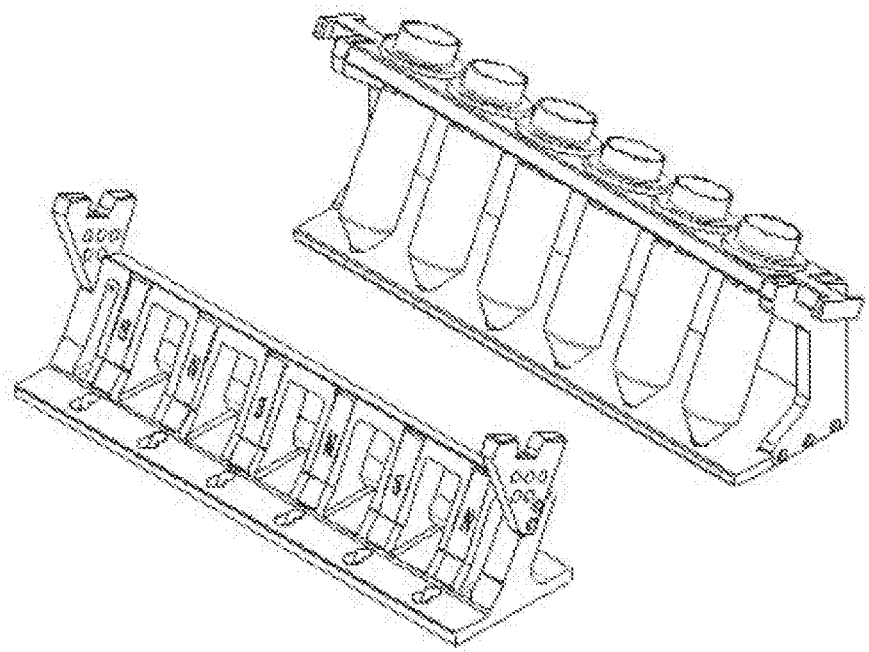
FIG. 8 is a working state diagram of a releasing process of magnetic beads of an inclined magnetic holder device according to the present invention.
Figure 9:
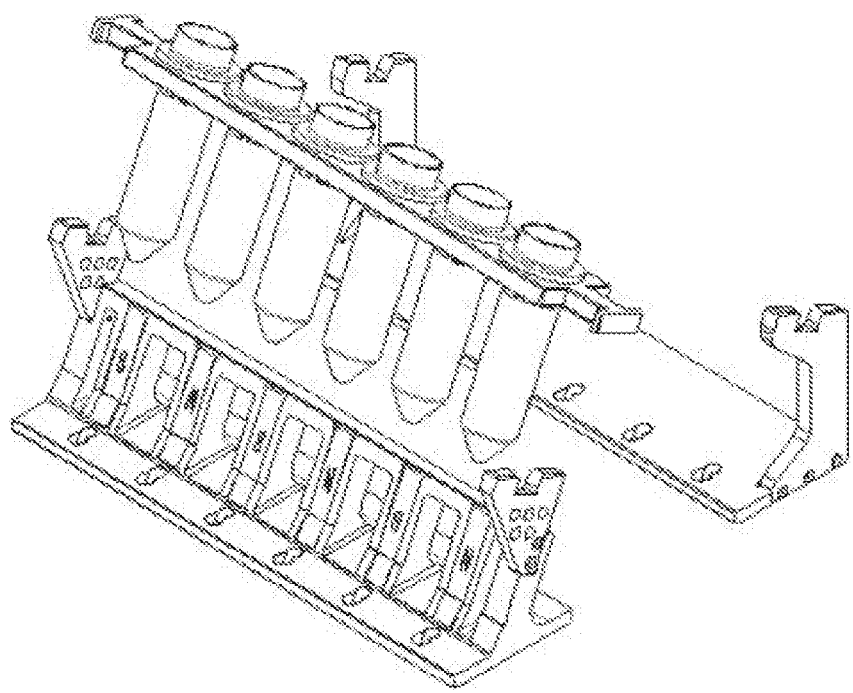
FIG. 9 is a working state diagram of separating or releasing magnetic beads of an inclined magnetic holder device according to the present invention.

A structure of an embodiment of an inclined magnetic holder device of the present invention is shown in FIG. 1 to FIG. 9. The inclined magnetic holder device in this embodiment includes a magnetic base 1, a nonmagnetic base 3, and a centrifugal tube supporting plate 2. Centrifugal tube supporting holes are provided on the centrifugal tube supporting plate 2. The centrifugal tube supporting holes are evenly distributed on the centrifugal tube supporting plate 2 in a straight line, that is, the centrifugal tube supporting holes are distributed in a single row. An annular elastic buckle 4 for fixing a centrifugal tube is installed in the centrifugal tube supporting hole. The elastic buckle 4 includes an annular ring 4-1. Locking feet 4-2 and clamping feet 4-3 are evenly distributed along the annular ring 4-1 at intervals, the locking feet 4-2 protrude outward from the annular ring for fixing on the centrifugal tube supporting hole, and the clamping feet 4-3 protrude inwards the annular ring for fixing the centrifugal tube. The numbers of the locking feet 4-2 and the clamping feet 4-3 in the elastic buckle 4 are greater than or equal to 3, and the material of the elastic buckles is PA66.

The magnetic base 1 includes a first baseplate 1-1, a fixing plate 1-2 disposed on the first baseplate 1-1 and two first side supporting plates 1-3 located at two sides of the fixing plate 1-2; positioning grooves 6 are respectively provided on the top of the two first side supporting plates 1-3; bottom surfaces 6-2 of the positioning grooves 6 are disposed inclinedly; positioning bumps 2-1 for engaging in the positioning grooves 6 are respectively provided at two ends of the centrifugal tube supporting plate 2. Handles 2-2 are respectively provided at the positioning bumps 2-1 at two ends of the centrifugal tube supporting plate 2. The positioning groove 6 has a cross section of a trapezoidal groove with a larger top and a smaller bottom, two sides of the trapezoidal groove are in the shape of bevels 6-1, the two sides of the positioning bumps 2-1 are provided with guiding bevels 2-11 engaging with the bevels 6-1 of the trapezoidal groove, and blocking surfaces 2-12 fit with a side plate blocking part are provided on two sides of the positioning bumps on the centrifugal tube supporting plate. A magnet sheet A7-1 is provided on a bottom surface of the positioning groove 6, a magnet sheet B7-2 for being absorbed with the magnet sheet A7-1 is provided on a bottom surface of the positioning bump 2-1, and adjacent surfaces of the magnet sheet A7-1 and the magnet sheet B7-2 have opposite polarities.

A bolt hole 1-31 is provided on the first side supporting plate 1-3, and the two first side supporting plates 1-3 are fixedly installed on the two sides of the fixing plate 1-2 via bolts 1-32. Magnet blocks 5 are respectively fixed on positions of the fixing plate 1-2 corresponding to the underneath of all of the centrifugal tube supporting holes; the magnet block 5 below each centrifugal tube supporting hole respectively corresponds to each centrifugal tube, and a surface where the N or S pole of the magnet block 5 is located faces the centrifugal tube and is parallel to the axis of the centrifugal tube. The number of the magnet blocks 5 is equal to that of the holes of the centrifugal tube supporting plate. In this embodiment, the number of the magnet blocks 5 is 6.

In this embodiment, the fixing plate 1-2 and the first baseplate 1-1 are integratedly connected together. The fixing plate 1-2 is disposed on the first baseplate 1-1 inclinedly; an angle of the fixing plate 1-2 is the same as that of a centrifugal tube installed in the centrifugal tube supporting plate 2; the magnet block 5 is L-shaped, the N or S pole of the L-shaped magnet block is located on the outer side of the vertical end of the L-shaped magnet block, the outer side of the vertical end of the L-shaped magnet block and the fixing plate are located in the same plane, and the lateral end of the L-shaped magnet block is fixed on the first baseplate 1-1. An angle between the fixing plate 1-2 and a horizontal surface is 90° to 135°. The magnet blocks with the N pole facing the centrifugal tube and the magnet blocks with the S pole facing the centrifugal tube are laid out in a manner where adjacent magnet blocks have opposite magnetic polarities. The layout manner is N-S-N-S-N-S or S-N-S-N-S-N. The material of the magnet block 5 is strong Nd—Fe—B magnet N52, and the surface of the magnet block is provided with a single-layer nickel bright silver anticorrosive layer.

The nonmagnetic base 3 includes a second baseplate 3-1 and two second side supporting plates 3-2 fixed on two sides of the second baseplate 3-1, and positioning grooves 6 engaged with the positioning bump 2-1 are provided on the top of the two second side supporting plates 3-2. The material of the first baseplate 1-1, the fixing plate 1-2, the first side supporting plate 1-3, the centrifugal tube supporting plate 2, the second baseplate 3-1, and the second side supporting plate 3-2 is all ABS plastic.

A centrifugal tube positioning hole 8 is provided on a position of the first baseplate 1-1 and the second baseplate 3-1 corresponding to the underneath of each of the centrifugal tube supporting holes. The centrifugal tube positioning hole 8 is a gourd-shaped hole, the gourd-shaped hole includes two circular holes with different diameters connected together in a front-to-back direction, and the axis of the two circular holes is parallel to the axis of the centrifugal tube.

When magnetic bead separation is performed, by using a magnetic holder of this embodiment, magnetic beads that can combine a to-be-separated sample are added to a centrifugal tube with the to-be-separated sample; the centrifugal tube is fixed in a centrifugal tube supporting hole via the elastic buckle. The elastic buckle is locked and fixed on the centrifugal tube supporting plate by the locking feet. The elastic buckle can clamp and fix a centrifugal tube of various sizes with the clamping feet. The centrifugal tubes within a size range of 15 ml to 100 ml are applicable. Handles at two ends of the centrifugal tube supporting plate are used to respectively install positioning bumps at two ends of the centrifugal tube supporting plate into the positioning grooves on two first side supporting plates. A guide bevel on a positioning bump of the centrifugal tube supporting plate is fitted with a bevel guide of a trapezoidal positioning groove. A blocking surface may prevent the centrifugal tube supporting plate from laterally moving, in combination with the magnetic absorption function of magnets A and B, which may easily assemble the centrifugal tube supporting plate with the centrifugal tube on the magnetic base. Because the bottom surfaces of the positioning grooves are inclinedly set, the assembled centrifugal tube supporting plate and centrifugal tube are inclinedly set. The inclined arrangement of the L-shaped magnet block with high magnetism and an arrangement manner where magnetic poles of adjacent magnet blocks are opposite greatly improve the efficiency of magnetic bead adsorption and reduce the loss of magnetic beads. When magnetic bead release operation is performed, positioning bumps at two ends of the centrifugal tube supporting plate are respectively installed in the positioning grooves on the two second side supporting plates, thereby easily implementing magnetic bead release operation by assembling the centrifugal tube supporting plate on the nonmagnetic base.

In the present invention, assembly or separation of the centrifugal tube supporting plate and the magnetic base can be easily achieved in the present invention. A user may synchronously perform magnetic separation, mixing operation, and waste liquid pouring in the purification of all samples and protein transfer after purification. The centrifugal tube supporting holes are evenly distributed on the centrifugal tube supporting plate along a straight line. The centrifugal tubes are arranged in a single row, and all waste liquid can be removed at one time by overall flipping, thereby greatly increasing efficiency of removing waste liquid, and avoiding sample cross-contamination between centrifugal tubes during the flipping process.

An inclined magnetic holder device provided in the present invention has the following advantages.

(1) A lightweight supporting plate is provided with an easy-to-operate handle. Magnetic beads that can combine to-be-separated samples are added to a centrifugal tube with the to-be-separated samples. By means of the magnetic absorption function of magnets A and B, a positioning groove of the first side supporting plate, and a guiding bevel of a positioning bump of the centrifugal tube supporting plate, it is easy to assemble the centrifugal tube supporting plate with the centrifugal tube onto the magnetic base for magnetic bead absorption or onto the nonmagnetic base for performing magnetic bead separation or release operation, thereby easily implementing separation of the centrifugal tube supporting plate, the magnetic base, and the nonmagnetic base. The user may synchronously perform magnetic separation, mixing operation, and waste liquid pouring in the purification of all samples and protein transfer after purification.

(2) Specially designed elastic buckles include locking feet and clamping feet. The elastic buckles can realize locking and fixing of the centrifugal tubes and the supporting plate with the locking feet. The elastic buckles can clamp and fix centrifugal tubes of different sizes with the clamping feet. During the process of flipping, shaking and pouring the waste liquid inclinedly, the centrifugal tube is prevented from loosening or falling off, and the centrifugal tubes are easily taken out and installed.

(3) Several L-shaped magnet blocks fixed by the specifically designed inclined magnetic base are inclined. After the centrifugal tube supporting plate is assembled with the inclined magnetic base, the centrifugal tubes are in inclined states corresponding to the L-shaped magnet blocks one-to-one. The L-shaped magnet blocks with the N pole facing the centrifugal tube and the L-shaped magnet blocks with the S pole facing the centrifugal tube are laid out in a manner where adjacent magnet blocks have opposite magnetic polarities. The layout manner is N-S-N-S-N-S or S-N-S-N-S-N. The layout positions of the L-shaped magnet block and the centrifugal tube in a height direction is more reasonable. The L-shaped magnet blocks are arranged in the above manner, which greatly increases the absorption efficiency of magnetic beads and reduces loss of magnetic beads.

(4) The special single-row arrangement of centrifugal tubes and the manner of overall pouring waste liquid by flipping can greatly improve the efficiency of removing the waste liquid, and completely avoid sample cross-contamination between centrifugal tubes during this process.

(5) A magnetic base has a specially inclined design, and the overall structure is simple and lightweight, which is convenient for installation and flexible operation.

The above embodiment is a preferred embodiment of the present invention. In other embodiments of the present invention, the number of the centrifugal tube supporting plate holes is 1 to 20. Preferably, the number of the holes of the centrifugal tube supporting plate is 4 to 12. More preferably, the number of the holes of the centrifugal tube supporting plate is 6 to 8.

In other embodiments of the present invention, a long strip structure may be used for the magnet block, and other magnet blocks of other shapes may be used, as long as a surface with the N or S pole facing the centrifugal tube is inclinedly set and is parallel to the axis of the centrifugal tube. Each centrifugal tube may correspond to multiple magnet blocks, and the multiple magnet blocks corresponding to each centrifugal tube are distributed in a length direction of the centrifugal tube.

In other embodiments of the present invention, other structures may be used for the elastic buckle, as long as the centrifugal tube is fixed to the centrifugal tube supporting hole.

The above description is only for explaining the technical concept and features of the present invention, and is not exhaustive for specific implementation manners, and cannot limit the protection scope of the present invention. Any equivalent replacement or change according to the technical solution of the present invention and its concept should be covered by the protection scope of the present invention, and the scope of the present invention defined by the appended claims includes all equivalent substitutions and changes.

The invention claimed is:

1. An inclined magnetic holder device, comprising a magnetic base and a centrifugal tube supporting plate having centrifugal tube supporting holes thereon, wherein the magnetic base comprises a first baseplate, a fixing plate disposed on the first baseplate, a first supporting plate located at a first side of the fixing plate, and a second supporting plate located at a second side of the fixing plate; positioning grooves of the magnetic base are respectively provided on the top of the first and second supporting plates; bottom surfaces of the positioning grooves of the magnetic base are disposed inclinedly; positioning bumps for engaging in the positioning grooves of the magnetic base are respectively provided at two ends of the centrifugal tube supporting plate; the centrifugal tube supporting holes are evenly distributed on the centrifugal tube supporting plate in a straight line; annular elastic buckles for fixing a centrifugal tube are installed in the centrifugal tube supporting holes; magnet blocks are respectively fixed on positions of the fixing plate corresponding to the underneath of all of the centrifugal tube supporting holes; the magnet block below each centrifugal tube supporting hole respectively corresponds to each centrifugal tube, and a surface where the N or S pole of the magnet block is located faces the centrifugal tube and is parallel to the axis of the centrifugal tube.

2. The inclined magnetic holder device according to claim 1, further comprising a nonmagnetic base, wherein the nonmagnetic base comprises a second baseplate, a first supporting plate of the nonmagnetic base fixed at a first side of the second baseplate, and a second supporting plate of the nonmagnetic base fixed at a second side of the second baseplate, and positioning grooves of the nonmagnetic base engaged with the positioning bumps of the centrifugal tube supporting plate are respectively provided on the top of the first and second supporting plates of the nonmagnetic base.

3. The inclined magnetic holder device according to claim 2, wherein a magnet sheet A is provided on a bottom surface of each positioning groove of the magnetic base, a magnet sheet B for being absorbed with the magnet sheet A is provided on a bottom surface of each positioning bump of the centrifugal tube supporting plate, and adjacent surfaces of the magnet sheet A and the magnet sheet B have opposite polarities.

4. The inclined magnetic holder device according to claim 2, wherein each positioning groove of the magnetic base has a cross section of a trapezoidal groove with a larger top and smaller bottom, wherein two sides of the trapezoidal groove are beveled, wherein each positioning bump of the centrifugal tube supporting plate has two sides which are provided with respective guiding bevels engaged with the two beveled sides of the trapezoidal groove, and wherein respective blocking surfaces fit with a side plate blocking part are provided on the two sides of each positioning bump on the centrifugal tube supporting plate.

5. The inclined magnetic holder device according to claim 2, wherein a centrifugal tube positioning hole is provided on a position of the first baseplate and the second baseplate corresponding to the underneath of each of the centrifugal tube supporting holes.

6. The inclined magnetic holder device according to claim 5, wherein the centrifugal tube positioning hole comprises two circular holes with different diameters connected together in a front-to-back direction, and the axis of the two circular holes is parallel to the axis of the centrifugal tube.

7. The inclined magnetic holder device according to claim 1, wherein the magnet blocks with the N pole facing the centrifugal tube and the magnet blocks with the S pole facing the centrifugal tube are laid out in a manner where adjacent magnet blocks have opposite magnetic polarities.

8. The inclined magnetic holder device according to claim 1, wherein the material of each of the magnet blocks is a strong Nd-Fe-B magnet N52, and the surface of each of the magnet blocks is provided with a single-layer nickel bright silver anticorrosive layer.

9. The inclined magnetic holder device according to claim 1, wherein the fixing plate is disposed inclinedly on the first baseplate; an angle of the fixing plate is the same as an angle of the centrifugal tube installed in the centrifugal tube supporting plate; each of the magnet blocks is L-shaped, and wherein for each of the L-shaped magnet blocks, the N or S pole of the L-shaped magnet block is located on an outer side of a vertical end of the L-shaped magnet block, the outer side of the vertical end of the L-shaped magnet block and the fixing plate are located in the same plane, and the lateral end of the L-shaped magnet block is fixed on the first baseplate.

10. The inclined magnetic holder device according to claim 9, wherein an angle between the fixing plate and a horizontal surface is 90° to 135°.

11. The inclined magnetic holder device according to claim 9, wherein the fixing plate and the first baseplate are integratedly connected together.

12. The inclined magnetic holder device according to claim 9, wherein the material of the first baseplate, the fixing plate, the first and second supporting plates of the magnetic base, and the centrifugal tube supporting plate is all ABS plastic.

13. The inclined magnetic holder device according to claim 1, wherein the elastic buckle comprises an annular ring, locking feet and clamping feet are evenly and distributed on the annular ring at intervals, the locking feet protrude outward from the annular ring for fixing on the centrifugal tube supporting holes, and the clamping feet protrude inwards the annular ring for fixing the centrifugal tube.

14. The inclined magnetic holder device according to claim 13, wherein the numbers of the locking feet and the clamping feet in the elastic buckle are greater than or equal to 3, and the material of the elastic buckles is the material PA66.

15. The inclined magnetic holder device according to claim 1, wherein the positioning bumps on the two ends of the centrifugal tube supporting plate are respectively provided with handles.

16. The inclined magnetic holder device according to claim 1, wherein respective bolt holes are provided on the first and second supporting plates, and the first and second supporting plates are fixedly installed on the first and second sides of the fixing plate via bolts respectively.

17. The inclined magnetic holder device according to claim 1, wherein the number of the holes of the centrifugal tube supporting plate is 1 to 20, and the number of the magnet blocks is equal to that of the holes of the centrifugal tube supporting plate.

18. The inclined magnetic holder device according to claim 17, wherein the number of the holes of the centrifugal tube supporting plate is 4 to 12.

19. The inclined magnetic holder device according to claim 2, wherein each positioning groove of the nonmagnetic base has a cross section of a trapezoidal groove with a larger top and smaller bottom, wherein two sides of the trapezoidal groove are beveled, wherein each positioning bump of the centrifugal tube supporting plate has two sides which are provided with respective guiding bevels engaged with the two beveled sides of the trapezoidal groove, and wherein respective blocking surfaces fit with a side plate blocking part are provided on the two sides of each positioning bump on the centrifugal tube supporting plate.

20. The inclined magnetic holder device according to claim 2, wherein the material of the first baseplate, the fixing plate, the first and second supporting plates of the magnetic base, the centrifugal tube supporting plate, the second baseplate, and the first and second supporting plates of the nonmagnetic base is all ABS plastic.

* * * * *